Figure 1:
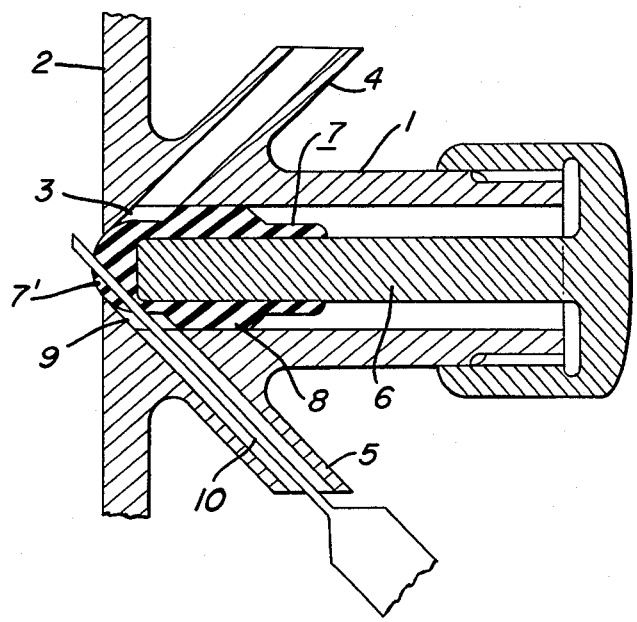

United States Patent [19]

Ottung

[11] 4,423,641
[45] Jan. 3, 1984

[54] SAMPLING VALVE FOR DRAWING SAMPLES FROM TANKS CONTAINING EASILY CONTAMINATED LIQUIDS

[76] Inventor: Kaj Ottung, Askebyvej 8, DK-2830 Virum, Denmark

[21] Appl. No.: 310,877

[22] Filed: Oct. 13, 1981

[30] Foreign Application Priority Data

Oct. 13, 1980 [DK] Denmark ............................. 4327/80

[51] Int. Cl.³ ............................................. G01N 1/10
[52] U.S. Cl. .............................. 73/863.86; 73/863.85; 137/240
[58] Field of Search ........... 73/863.81, 863.85, 863.86; 137/240

[56] References Cited

U.S. PATENT DOCUMENTS

| 3,334,648 | 8/1967 | Probst | 137/240 X |
| 3,412,613 | 11/1968 | Brown et al. | 73/863.85 |
| 3,638,499 | 2/1972 | Saint-Andre | 73/863.86 |
| 3,779,082 | 12/1973 | Galloway | 73/863.85 |
| 3,834,415 | 9/1974 | Herron | 137/240 X |
| 3,930,413 | 1/1976 | Laird et al. | 73/863.85 |
| 4,199,988 | 4/1980 | Riegger | 73/863.81 |
| 4,359,908 | 11/1982 | Perras | 73/863.85 |

FOREIGN PATENT DOCUMENTS 1175015 7/1964 Fed. Rep. of Germany ... 73/863.81

Primary Examiner—Herbert Goldstein
Assistant Examiner—Tom Noland
Attorney, Agent, or Firm—Wayne B. Easton

[57] ABSTRACT

The invention relates to a sampling valve for drawing samples from a tank containing easily contaminated liquids. The valve closure member is of a material that is pierceable by a hypodermic needle. An outlet port is arranged so that a hypodermic needle may be inserted through such port and likewise through the closure member and the valve seat while the closure member closingly engages the valve seat. A sample is thus drawable through the hypodermic needle despite the valve being otherwise closed by reason of the closure member being in engagement with the valve seat.

1 Claim, 1 Drawing Figure

SAMPLING VALVE FOR DRAWING SAMPLES FROM TANKS CONTAINING EASILY CONTAMINATED LIQUIDS

The invention relates to a sampling valve for drawing samples from tanks containing easily contaminated liquids. The valve comprises a valve housing with a conical valve seat, a valve spindle, one end of which is furnished with a handle, the other end with a valve body which, together with the valve seat, serve to open and close the valve, and two opposing hose-pieces fixed on the valve housing, and which are connected to each other via a ring-shaped channel between the inner side of the valve housing and the valve body.

In U.S. Pat. No. 3,334,648 there is described a valve for drawing liquid samples which comprises a valve housing, a valve spindle with a valve body which tightens against a valve seat, and two diametrically opposed hose-pieces, designed for cleaning the valve when it is not in use and for drawing off liquid when the valve is open, since the hose-pieces are interconnected by an annular space between the valve housing and the valve body.

It is known, similarly, that rubber membranes are used through which small amounts of liquid can be drawn by means of a hypodermic needle for microscopical examination. When it is desired to draw from a vessel both large amounts and small amounts of an easily injected liquid in a sterile state, it has been necessary until now to use a sterilizable valve, for example, of the type mentioned above, and a separate rubber membrane which is expensive and impracticable.

The purpose of the present invention is to achieve a sterilizable sampling valve of simple construction, through which it is possible to draw a large volume of samples by opening the valve, and to draw smaller microbiological samples through a rubber membrane in the valve when the valve is closed.

This aim is achieved by the sampling valve described at the beginning of this application, the novel characteristics of which are that the valve body is formed as a pierceable rubber body with a hole part which closes tightly around the spindle and compresses against the inner side of the valve housing and a solid part which is arranged to tighten against the valve seat and has a smaller diameter than that part of the rubber body which tightens against the inner side of the valve housing, and that the hose-pieces are situated so that their central axes intersect each other at the center of the valve seat.

The invention is illustrated in the drawing enclosed, where FIG. 1 shows a vertical section of the sampling valve in closed position and a hypodermic needle piercing the rubber body.

The valve housing 2 which may be welded to the wall of a vessel has a conical valve seat 3 and two hose-pieces 4 and 5. The valve spindle 6 is furnished with a rubber body 7' which tightens against the conical seat. The central part 8 of the rubber body tightens against the inner side of the valve housing while the solid part of the rubber body has a smaller diameter portion 7', so that an annular channel 9 is formed between the rubber body and the valve housing which connects the two hose-pieces, the central axes of which intersect at the center of the valve seat.

A hypodermic needle 10 is pushed through one of the hose-pieces 4 or 5 and through the rubber body 7 when small samples are drawn.

When the sampling valve is not in use, the two hose-pieces 4 and 5 can be connected by rubber tubing filled with alcohol, so that the annular channel 9 and the two hose-pieces remain filled with alcohol. When the rubber tubing is removed, a larger sample may be drawn without further sterilizing.

It is claimed:

1. A sampling valve for drawing sterile samples, from vessels containing liquids that are easily contaminated, comprising, a valve housing with a side to be flushly attached to one of said vessels, said side containing a conical valve seat, said housing defining a bore aligned with said valve seat, a valve unit in said bore having a spindle with a resilient body at one end thereof cooperable with said valve seat, said resilient body having a first part in sealing engagement with said bore and a second part of lesser diameter cooperable with said valve seat, a section of said housing including two externally accessible passages which are inclined relative to said bore and have axes which intersect at the center of said valve seat, said valve body second part being the part that closes said valve seat, said first part of said valve body and parts of said section which connect said two passages cooperating when said valve seat is closed to form an annular passage interconnecting said two externally accessible passages, said valve body second part being piercable, when said valve seat is closed, by a hypodermic needle first extending through either of said two externally accessible passages and thereafter through said annular passage.

* * * * *